United States Patent [19]

Vaerman

[11] Patent Number: 4,536,654
[45] Date of Patent: Aug. 20, 1985

[54] DEVICE FOR DETECTING FLAWS ON A PIECE

[75] Inventor: Jean F. Vaerman, Vert St Denis, France

[73] Assignee: Societe Nationale D'Etude et de Construction de Moteurs D'Aviation, Paris, France

[21] Appl. No.: 487,108

[22] Filed: Apr. 21, 1983

[30] Foreign Application Priority Data

Apr. 27, 1982 [FR] France .................. 82 07202

[51] Int. Cl.³ .......................................... G01N 21/27
[52] U.S. Cl. .................................. 250/458.1; 250/302; 250/461.1
[58] Field of Search .................. 250/302, 461.1, 461.2, 250/458.1, 358.1, 563; 350/6.8; 356/237, 317, 318

[56] References Cited

U.S. PATENT DOCUMENTS 3,774,030  8/1981  O'Connor et al. .......... 250/302
4,087,685  5/1978  Froot ........................ 250/302
4,162,405  7/1974  Chance et al. ............... 250/461.2
4,284,897  8/1981  Sawamura et al. ........... 250/461.2
4,428,672  1/1984  Allard et al. ................ 250/302

FOREIGN PATENT DOCUMENTS 0050935  5/1982  European Pat. Off. .
2044921  10/1980  United Kingdom .

Primary Examiner—Alfred E. Smith
Assistant Examiner—Carolyn E. Fields
Attorney, Agent, or Firm—Oblon, Fisher, Spivak, McClelland & Maier

[57] ABSTRACT

A device automatically reads indications of flaws in a piece using the sweating method. An ultraviolet beam illuminates the piece to be checked after successive reflections on a separating mirror and on two oscillating mirrors for sweeping. The beam reemitted parallel to the incident beam traverses the separating mirror and is received by a detector, the output information of which is transmitted to a data processing unit which also receives information on the position of the oscillating mirror over a different path.

7 Claims, 1 Drawing Figure

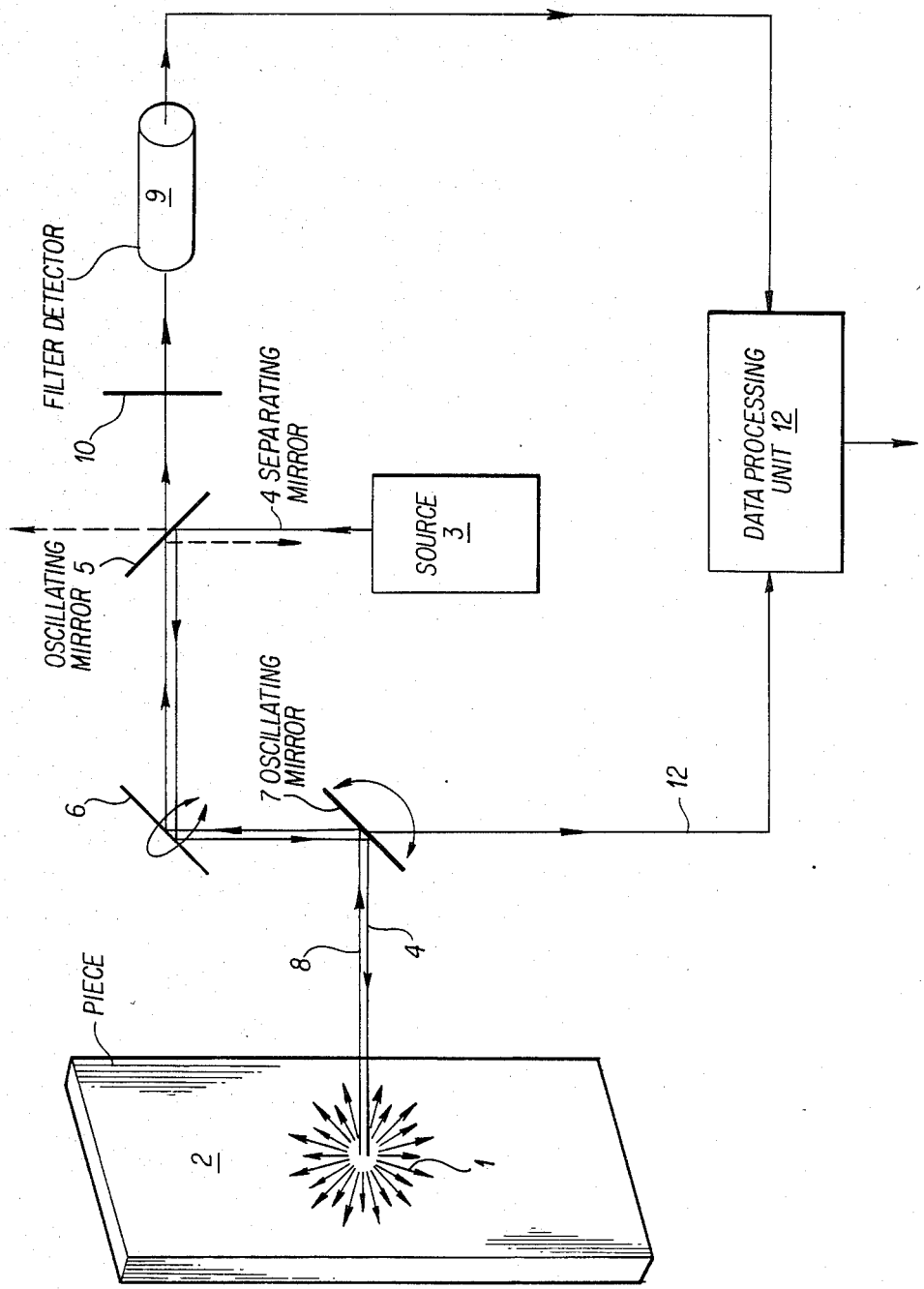

DEVICE FOR DETECTING FLAWS ON A PIECE

BACKGROUND OF THE INVENTION

1. Field of the Invention

The invention relates to a device for detecting flaws on a piece by the automatic reading of indications representative of the flaws to be detected given by a liquid which under the action of a radiation of a first wavelength reemits a radiation of a second wavelength.

2. Description of the Prior Art

It is well-known in monitoring methods that flaws in pieces, especially cracks and splits, can be shown by a special liquid which, under the action of a light, generally in the ultraviolet range, reemits a visible light usually located in the yellow-green range of colors. These known methods of visualizing flaws are called sweating or magnetoscopic methods depending on the method used to obtain the visualization of the flaws by the liquid.

These methods permit a convenient visual examination of the pieces to be performed. An automatic examination of the indications given by these methods has likewise already been proposed. To this end, the use of apparatuses is known which are composed of a monochromatic source emitting a fine ultraviolet beam which illuminates the piece to be studied, after being reflected on a separating mirror which reflects only ultraviolet rays and not visible light. The piece reemits a visible radiation which is not deflected by the separating mirror and is picked up by a detector placed in back of the mirror.

It is necessary in such devices to proceed to an analysis along two axes of the surface to be examined, which generally results in moving the piece during the operation and in using a complex detector.

SUMMARY OF THE INVENTION

Accordingly, one object of this invention is to provide a novel device of the type indicated above in which the monochromatic source emits a focused beam and a set of oscillating mirrors placed between the separating mirror and the piece simultaneously assure on the one hand the sweeping of the piece along two coordinate axes by the incident beam and on the other hand the directing onto the detector of the beam of light reemitted parallel to the incident beam.

The incident beam from the monochromatic source is advantageously in the ultraviolet range and the monochromatic source can be a laser or an ultraviolet lamp with the reemitted light being visible light.

According to a preferred embodiment of the invention the detector is followed by a data processing unit which also receives information on the position of the oscillating mirrors over a different path.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying FIGURE which illustrates a device for detecting flaws according to the present invention.

DETAILED DESCRIPTION OF THE PREFERRED EMBODIMENT

In the example shown, flaws 1 of piece 2 to be studied are visualized in a known manner, e.g. by the previously referred to sweating method, by means of a special liquid (not shown) which reemits a visible fluorescent light under the action of ultraviolet rays.

According to the invention a source 3 emits focused beam 4, the wavelength of which corresponds to ultraviolet light. This source 3, which is preferably but not necessarily monochromatic, is constituted by a laser or, more simply, by an ultraviolet lamp.

Beam 4 from source 3 is reflected 90° by separating mirror 5 which has the property of reflecting ultraviolet rays but not visible light.

After it has been reflected on separating mirror 5, ray 4 is successively reflected by two oscillating mirrors 6 and 7 which assure a sweeping along two axes of piece 2. Thus, the entire surface to be examined is swept by ultraviolet beam 4.

When ultraviolet beam 4 encounters a flaw 1 on piece 2 visualized by the presence of the liquid, the liquid reemits a visible, fluorescent light of a yellow-green color in all directions. From these beams of visible light reemitted at each point in all directions, the one which is parallel to the incident beam is successively picked up by oscillating mirrors 6 and 7 and directed onto separating mirror 5. However, since this beam 8 is constituted by visible light, it is not reflected and traverses this separating mirror 5 and is received by detector element 9 of the photoelectric type.

A filter 10 can be placed between separating mirror 5 and detector element 9 which filter is centered on the wavelength of the visible light reemitted and totally eliminates the residual ultraviolet rays which could influence the detector and furnish false information.

The information of detector 9 is transmitted to data processing unit 11, which also receives information on the position of mirrors 6 and 7, schematically shown via path 12, and therefore on the location of piece 2 at a given instant.

The device of the invention is relatively simple, because of the optical sweeping system which is used simultaneously for the two beams, incident and reemitted. Thus the piece, the source and the detector can be fixed.

This example was described using an ultraviolet incident beam and a reemitted beam of visible light. It is obvious that the invention could also be accomplished using other beams, with the sole condition that the wavelengths are different for each beam. This depends solely on the liquid used for visualizing the flaws. The separating mirror is then adapted to reflect one of the wavelengths and to let the second one pass through.

Obviously, numerous (additional) modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. In a device for detecting flaws on a piece by the automatic reading of indications representative of the flaws to be detected which indications are given by a liquid which, under the action of a light of a first wavelength, emits a radiation of light of a second wavelength, said device being of the type having a source which emits a beam of light of the first wavelength which illuminates the piece to be studied, after said first wavelength beam is reflected by a separating mirror which separating mirror reflects said light of the first wavelength and passes said light of the second wavelength, and with a portion of the light of said second wavelength emitted by said liquid forming a beam which is parallel to and in the opposite direction from said beam of light of the first wavelength reflected by said separating mirror and with said second wavelength beam being detected by a detector, the improvement comprising:

said source emitting a focused beam; and first and second oscillating mirrors placed between said separating mirror and said piece to simultaneously assure on the one hand the sweeping of the piece along two coordinate axes by the first wavelength beam and on the other hand the directing onto the detector of said second wavelength beam emitted by said liquid parallel to and in the opposite direction from said first wavelength beam.

2. Device for detecting flaws according to claim 1, wherein said first wavelength corresponds to ultraviolet light and said second wavelength corresponds to visible light.

3. Device for detecting flaws according to any one of claims 1 and 2, wherein said detector outputs a signal to a data processing unit which also receives information on the position of said oscillating mirrors over a different path.

4. Device for detecting flaws according to any one of claims 1 and 2, further comprising a filter means placed between said separating mirror and said detector which allows the light of the second wavelength to pass and blocks the residual rays of the first wavelength.

5. Device for detecting flaws according to any one of claims 1 and 2, wherein said source is monochromatic.

6. Device for detecting flaws according to any one of claims 1 and 2, wherein, said source is an ultraviolet lamp.

7. Device for detecting flaws according to claim 1, wherein said source is a laser device.

* * * * *